US012646151B2

(12) United States Patent
Wang et al.

(10) Patent No.: US 12,646,151 B2
(45) Date of Patent: Jun. 2, 2026

(54) METHODS AND SYSTEMS FOR FLEXIBLE DENOISING OF IMAGES USING DISENTANGLED FEATURE REPRESENTATION FIELD

(71) Applicant: KONINKLIJKE PHILIPS N.V., Eindhoven (NL)

(72) Inventors: Xin Wang, Belmont, NY (US); Saifeng Liu, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 323 days.

(21) Appl. No.: 18/267,606

(22) PCT Filed: Dec. 10, 2021

(86) PCT No.: PCT/EP2021/085120
§ 371 (c)(1),
(2) Date: Jun. 15, 2023

(87) PCT Pub. No.: WO2022/128758
PCT Pub. Date: Jun. 23, 2022

(65) Prior Publication Data
US 2024/0104700 A1 Mar. 28, 2024

Related U.S. Application Data

(60) Provisional application No. 63/127,424, filed on Dec. 18, 2020.

(51) Int. Cl.
*G06T 5/70* (2024.01)
*G06T 7/00* (2017.01)
(Continued)

(52) U.S. Cl.
CPC .............. *G06T 5/70* (2024.01); *G06T 7/0002* (2013.01); *G06T 7/10* (2017.01); *G06V 10/44* (2022.01);
(Continued)

(58) Field of Classification Search
CPC G06T 5/70; G06T 7/0002; G06T 7/10; G06T 2207/20081; G06T 2207/30168;
(Continued)

(56) References Cited

U.S. PATENT DOCUMENTS 10,949,951 B2 3/2021 Tang
11,030,723 B2 6/2021 Kamio
(Continued)

FOREIGN PATENT DOCUMENTS

JP 2020166814 A 10/2020

OTHER PUBLICATIONS

PCT International Search Report, International application No. PCT/EP2021/084465, Feb. 22, 2022.
(Continued)

*Primary Examiner* — Jennifer Mehmood
*Assistant Examiner* — Pardis Sohraby
(74) *Attorney, Agent, or Firm* — Larry Liberchuk

(57) ABSTRACT

A system and method are provided for denoising images. A standard image module is configured to generate a standard anatomy feature and a standard noise feature from a standard image and reconstruct the standard image from the standard anatomy feature and the standard noise feature. A reduced quality image module is configured to generate a reduced quality anatomy feature and a reduced quality noise feature from a reduced quality image, and reconstruct the reduced quality image from the reduced quality anatomy feature and the reduced quality noise feature. A loss calculation module is provided for calculating loss metrics at least partially
(Continued)

based on a comparison between 1) the reconstructed standard image and the standard image, and 2) the reconstructed reduced quality image and the reduced quality image. Upon providing the standard image module with the reduced quality anatomy feature, the standard image module outputs a reconstructed standard transfer image.

20 Claims, 7 Drawing Sheets

(51) Int. Cl.
  *G06T 7/10*     (2017.01)
  *G06V 10/44*     (2022.01)
  *G16H 30/40*     (2018.01)

(52) U.S. Cl.
  CPC ... *G16H 30/40* (2018.01); *G06T 2207/20081* (2013.01); *G06T 2207/30168* (2013.01)

(58) Field of Classification Search
  CPC ............. G06T 5/60; G06T 2207/10081; G06T 2207/20084; G06T 2207/30004; G06V 10/44; G16H 30/40; G06N 3/0455; G06N 3/0464; G06N 3/0475; G06N 3/09; G06N 3/094; G06N 3/045; G06N 3/08; G06N 3/096
  USPC ........................................................ 382/275
  See application file for complete search history.

(56)       References Cited

U.S. PATENT DOCUMENTS

| | | | |
|---|---|---|---|
| 11,501,438 B2 | 11/2022 | Xu | |
| 11,983,846 B2 | 5/2024 | Dangi | |
| 2015/0254850 A1* | 9/2015 | Jorgensen .............. | A61B 5/489 |
| | | | 382/133 |
| 2016/0071245 A1* | 3/2016 | Bergner ................... | G06T 5/70 |
| | | | 382/131 |
| 2020/0175662 A1* | 6/2020 | Wang ....................... | A61B 6/03 |

OTHER PUBLICATIONS

Huang Yongqiang et al: "Noise-Powered Disentangled Representation for Unsupervised Speckle Reduction of Optical Coherence Tomography Images", IEEE Transactions on Medical Imaging, IEEE, USA, vol. 40, No. 10, Dec. 16, 2020 (Dec. 16, 2020), pp. 2600-2614, XP011880799.
Zhang Zizhao et al: "Translating and Segmenting Multimodal Medical vols. with Cycle- and Shape- Consistency Generative Adversarial Network", 2018 IEEE/CVF Conference on Computer Vision and Pattern Recognition, IEEE, Jun. 18, 2018 (Jun. 18, 2018), pp. 9242-9251, XP033473850.
Shizuo Kaji et al: "Overview of image-to-image translation by use of deep neural networks: denoising, super-resolution, modality conversion, and reconstruction in medical imaging", arxiv.org, Cornell University Library, 201 Olin Library Cornell University Ithaca, NY 14853, May 21, 2019 (May 21, 2019), XP081371192.
Zhang R. et al., "The Unreasonable Effectiveness of Deep Features as a Perceptual Metric", 2018 IEEE/CVF Conference on Computer Vision and Pattern Recognition, 2018, p. 586-595.

* cited by examiner

METHODS AND SYSTEMS FOR FLEXIBLE DENOISING OF IMAGES USING DISENTANGLED FEATURE REPRESENTATION FIELD

The present disclosure generally relates to systems and methods for training and tuning neural network models for providing flexible solutions for denoising low dose images using domain-agnostic learning with disentangled feature representation.

BACKGROUND

Conventionally, in most imaging modalities there are effects in the acquisition physics or reconstruction that lead to artifacts, such as noise, in the final image. In order to train a denoising algorithm, such as a neural network model, pairs of noisy and noiseless image samples are presented to the neural network model and the network attempts to minimize a cost function by denoising the noisy image to recover a corresponding noiseless ground truth image.

However, any change in parameters used to acquire an image may result in changes in the form, or amount, of artifacts in the corresponding image. As such, a denoising model used to denoise a standard image is less effective when applied to an image acquired using different acquisition parameters, such as a reduced radiation dose in the context of a Computed Tomography (CT) scan.

The growing use of CT scans in modern medical practice has raised concerns over the associated radiation dose required, and dose reduction has become a clinical goal. However, lowering the radiation dose tends to significantly increase noise, and other artifacts, in reconstructed images, which may compromise diagnostic information. Extensive efforts have been made to reduce noise in low-dose CT scans and thereby convert them to images of superior quality.

Machine learning techniques, including the use of Convolutional Neural Networks (CNNs) have been studied in the context of image denoising. However, existing methods are typically tailored to specific noise levels and do not generalize well to noise levels not covered in a training set used to train the corresponding CNN.

In CT imaging, multiple factors, including Kilovoltage peak (kVp), Milliampere-Seconds (mAs), slice thickness, and patient size all may affect the noise level in a reconstructed image. The result that varying any of these imaging parameters may thereby result in different noise levels, or different artifact profiles, therefore traditionally requires a different model to denoise images acquired with such distinct imaging parameters. This limits the applicability of CNN based methods in practical denoising.

There is therefore a need for a method capable of denoising images acquired with imaging parameters different than those used in a training set for the corresponding method. There is a further need for a single trained model that can be used to denoise images with different noise levels, including CT images acquired with a lower radiation dose than the images of the training set.

SUMMARY

Systems and methods for denoising medical images are provided. In one embodiment, a standard image module is configured to generate a standard anatomy feature and a standard noise feature from a standard image, and reconstruct the standard image from the standard anatomy feature and the standard noise feature. A reduced quality image module is similarly configured to generate a reduced quality anatomy feature and a reduced quality noise feature from a reduced quality image, and reconstruct the reduced quality image from the reduced quality anatomy feature and the reduced quality noise feature.

A loss calculation module is provided such that the system and method can be trained. The loss calculation module is typically for calculating loss metrics at least partially based on a comparison between 1) the reconstructed standard image and the standard image, and 2) the reconstructed reduced quality image and the reduced quality image.

The loss metrics calculated at the loss calculation module are incorporated into loss functions for tuning the standard image module and the reduced quality image module using machine learning. Upon providing the standard image module with the reduced quality anatomy feature, the standard image module outputs a reconstructed standard transfer image that includes the reduced quality anatomy feature and a noise level lower than that represented by the reduced quality noise feature.

In some embodiments, the standard image module comprises a standard anatomy encoder, a standard noise encoder, and a standard generator, and upon receipt of the standard image, the standard anatomy encoder outputs the standard anatomy feature, the standard noise encoder outputs the standard noise feature, and the standard generator reconstructs the standard image from the standard anatomy feature and the standard noise feature.

In some such embodiments, the reduced quality image module may similarly comprise a reduced quality anatomy encoder, a reduced quality noise encoder, and a reduced quality generator, and upon receipt of the reduced quality image, the reduced quality anatomy encoder outputs the reduced quality anatomy feature, the reduced quality noise encoder outputs the reduced quality noise feature, and the reduced quality generator reconstructs the reduced quality image from the reduced quality anatomy feature and the reduced quality noise feature.

In some such embodiments, the loss calculation module calculates a loss metric for the standard generator at least partially based on the comparison between the reconstructed standard image and the standard image. Similarly, the loss calculation module may calculate a loss metric for the reduced quality generator at least partially based on the comparison between the reconstructed reduced quality image and the reduced quality image.

The loss calculation module may further calculate a loss metric for the standard anatomy encoder based on a comparison with segmentation labels for the standard image, and the loss calculation module may further calculate a loss metric for the reduced quality anatomy encoder based on a comparison with the output of the standard anatomy encoder.

In some embodiments, the loss metric for the reduced quality anatomy encoder is an adversarial loss metric.

In some embodiments a system implementing the described method may further comprise a segmentation network, and a segmentation mask for the reconstructed standard image may be evaluated based on a comparison with segmentation labels for the standard image.

In some such embodiments, upon providing the reduced quality generator with a standard anatomy feature, the reduced quality generator outputs a reconstructed reduced quality transfer image, the reduced quality transfer image including the standard anatomy features and a noise level higher than that represented by the standard noise feature. A segmentation mask for the reduced quality transfer image is then evaluated based on a comparison with the segmentation labels for the standard image.

In some embodiments, a loss metric for the standard transfer image is evaluated based on a comparison with a standard image reconstruction, and the loss metric for the standard transfer image is an adversarial loss metric.

In some embodiments, the standard image module and the reduced quality image module are trained simultaneously.

In other embodiments, the standard image module is trained prior to the training of the reduced quality image module, and values for variables developed while training the standard image module are held constant during training of the reduced quality image module. In some such embodiments, after training the standard image module and the reduced quality image module, the system further trains the standard generator while holding constant values for the standard anatomy encoder, the standard noise encoder, and the reduced quality anatomy encoder.

In some embodiments, the standard anatomy feature and the reduced quality anatomy feature each correspond to a single anatomical structure.

DETAILED DESCRIPTION OF THE PREFERRED EMBODIMENTS

Figure 1:
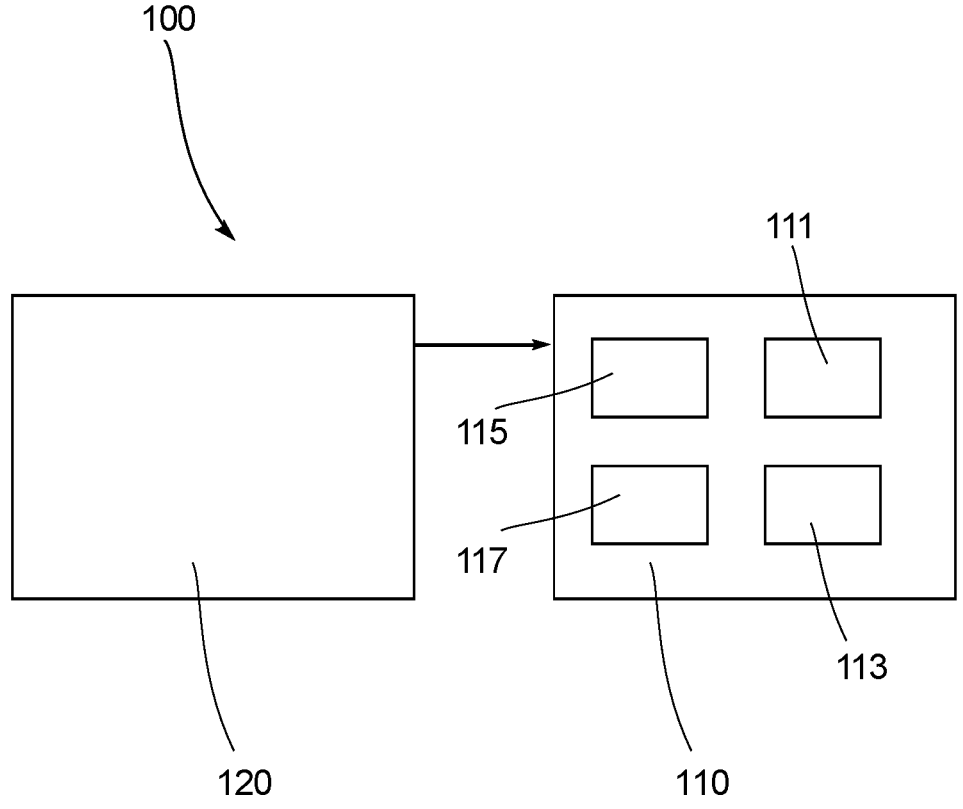
FIG. 1 is a schematic diagram of a system according to one embodiment of the present disclosure.

The description of illustrative embodiments according to principles of the present disclosure is intended to be read in connection with the accompanying drawings, which are to be considered part of the entire written description. In the description of embodiments of the disclosure disclosed herein, any reference to direction or orientation is merely intended for convenience of description and is not intended in any way to limit the scope of the present disclosure. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the disclosure are illustrated by reference to the exemplified embodiments. Accordingly, the disclosure expressly should not be limited to such exemplary embodiments illustrating some possible non-limiting combination of features that may exist alone or in other combinations of features; the scope of the disclosure being defined by the claims appended hereto.

This disclosure describes the best mode or modes of practicing the disclosure as presently contemplated. This description is not intended to be understood in a limiting sense, but provides an example of the disclosure presented solely for illustrative purposes by reference to the accompanying drawings to advise one of ordinary skill in the art of the advantages and construction of the disclosure. In the various views of the drawings, like reference characters designate like or similar parts.

It is important to note that the embodiments disclosed are only examples of the many advantageous uses of the innovative teachings herein. In general, statements made in the specification of the present application do not necessarily limit any of the various claimed disclosures. Moreover, some statements may apply to some inventive features but not to others. In general, unless otherwise indicated, singular elements may be in plural and vice versa with no loss of generality.

Generally, in order to denoise a medical image, an image processor, which may use an algorithm or model to denoise the image, is based on a level and form of noise expected to be present in the corresponding image. This level and form of expected noise is typically based on various parameters used to acquire an image.

In the context of Computed Tomography (CT) based medical imaging, for example, different image processors, such as machine learning algorithms which may take the form of Convolutional Neural Networks (CNNs), may be used to process images. These image processors are then trained, in the case of machine learning algorithms, on corresponding different anatomical regions and structures having a particular noise level. The noise level in the images may then be a function of multiple factors, including Kilovoltage peak (kVp), Milliampere-Seconds (mAs), slice thickness, and patient size.

While a denoising image processor, such as a CNN, may then be based on an expected noise level and form based on standardized parameters, including a standardized radiation dose, the systems and methods disclosed herein may effectively apply such a model to images acquired using different acquisition parameters, such as a reduced radiation dose.

While the discussion that follows is specific to implementations in CT based medical imaging, similar systems and methods may be used in the context of other imaging modalities, such as Magnetic Resonance Imaging (MRI) or Positron Emission Tomography (PET).

FIG. 1 is a schematic diagram of a system 100 according to one embodiment of the present disclosure. As shown, the system 100 typically includes a processing device 110 and an imaging device 120.

The processing device 110 may apply processing routines to images received. The processing device 110 may include a memory 113 and processor circuitry 111. The memory 113 may store a plurality of instructions. The processor circuitry 111 may couple to the memory 113 and may be configured to execute the instructions. The instructions stored in the memory 113 may comprise processing routines, as well as data associated with multiple machine learning algorithms, such as various Convolutional Neural Networks for processing images.

The processing device 110 may further include an input 115 and an output 117. The input 115 may receive information, such as images, from the imaging device 120. The output 117 may output information to a user or a user interface device. The output 117 may include a monitor or display.

In some embodiments, the processing device 110 may relate to the imaging device 120 directly. In alternate embodiments, the processing device 110 may be distinct from the imaging device 120, such that it receives images for processing by way of a network or other interface at the input 115.

In some embodiments, the imaging device 120 may include an image data processing device, and a spectral or conventional CT scanning unit for generating the CT projection data when scanning an object (e.g., a patient).

Figure 2:
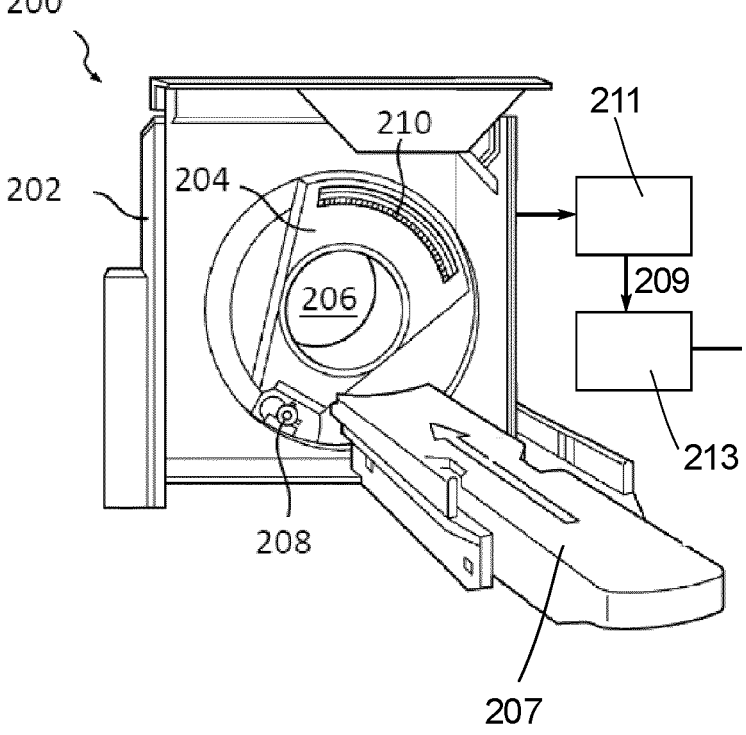
FIG. 2 illustrates an imaging device according to one embodiment of the present disclosure.

FIG. 2 illustrates an exemplary imaging device according to one embodiment of the present disclosure. It will be understood that while a CT imaging device is shown, and the following discussion is in the context of CT images, similar methods may be applied in the context of other imaging devices, and images to which these methods may be applied may be acquired in a wide variety of ways.

In an imaging device in accordance with embodiments of the present disclosure, the CT scanning unit may be adapted for performing multiple axial scans and/or a helical scan of an object in order to generate the CT projection data. In an imaging device in accordance with embodiments of the present disclosure, the CT scanning unit may comprise an energy-resolving photon counting image detector. The CT scanning unit may include a radiation source that emits radiation for traversing the object when acquiring the projection data.

Further, in an imaging device in accordance with embodiments of the present disclosure, the CT scanning unit may perform scout scans distinct from primary scans, thereby generating distinct images associated with a scout scan and a primary scan, where the images are different but comprise the same subject matter.

In the example shown in FIG. 2, the CT scanning unit 200, e.g. the Computed Tomography (CT) scanner, may include a stationary gantry 202 and a rotating gantry 204, which may be rotatably supported by the stationary gantry 202. The rotating gantry 204 may rotate, about a longitudinal axis, around an examination region 206 for the object when acquiring the projection data. The CT scanning unit 200 may include a support 207 to support the patient in the examination region 206 and configured to pass the patient through the examination region during the imaging process.

The CT scanning unit 200 may include a radiation source 208, such as an X-ray tube, which may be supported by and configured to rotate with the rotating gantry 204. The radiation source 208 may include an anode and a cathode. A source voltage applied across the anode and the cathode may accelerate electrons from the cathode to the anode. The electron flow may provide a current flow from the cathode to the anode, such as to produce radiation for traversing the examination region 206.

The CT scanning unit 200 may comprise a detector 210. The detector 210 may subtend an angular arc opposite the examination region 206 relative to the radiation source 208. The detector 210 may include a one or two dimensional array of pixels, such as direct conversion detector pixels. The detector 210 may be adapted for detecting radiation traversing the examination region and for generating a signal indicative of an energy thereof.

The CT scanning unit 200 may further include generators 211 and 213. The generator 211 may generate tomographic projection data 209 based on the signal from the detector 210. The generator 213 may receive the tomographic projection data 209 and generate a raw image of the object based on the tomographic projection data 209.

Figure 3:
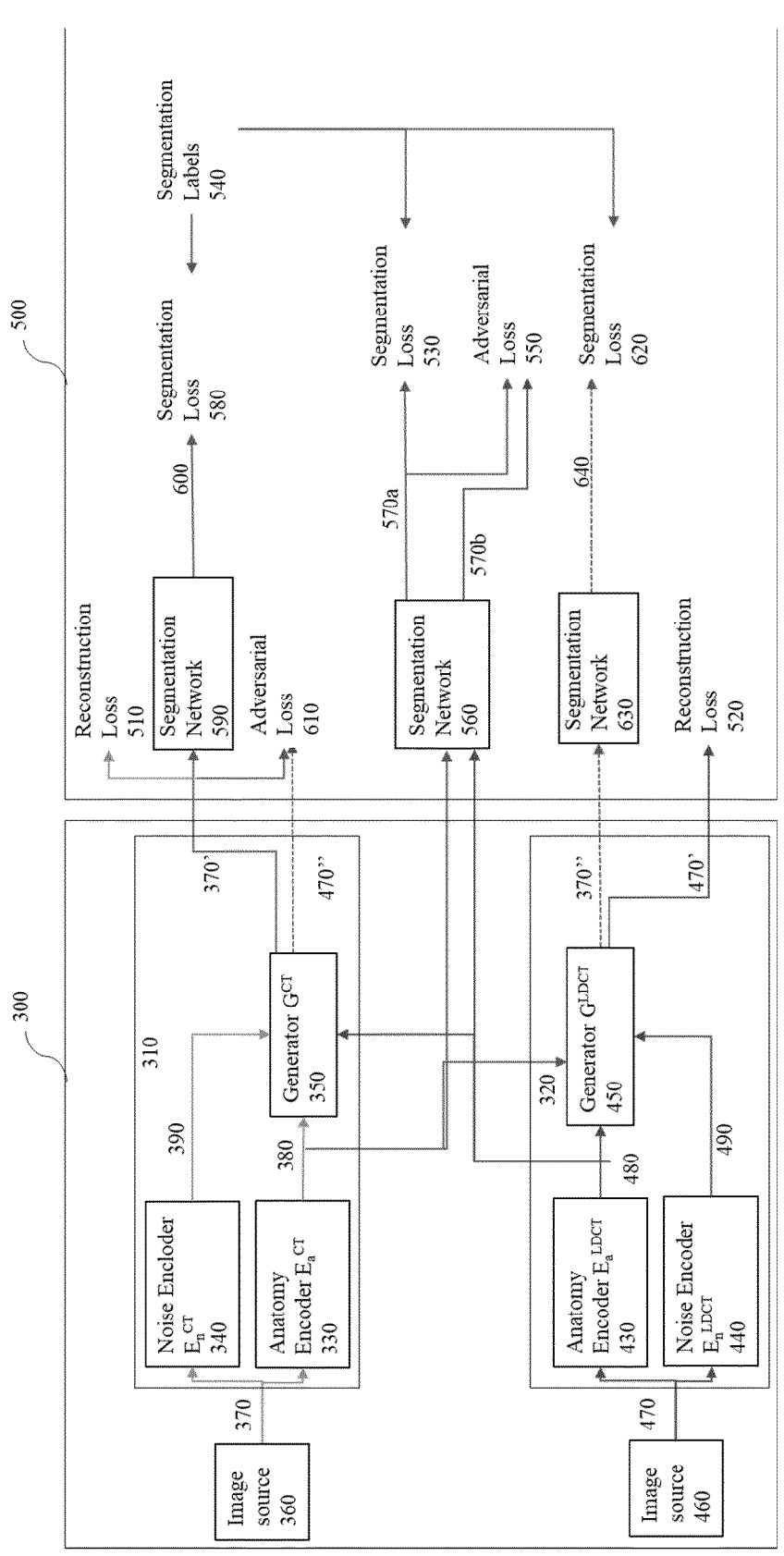
FIG. 3 is a training pipeline for use in an embodiment of the present disclosure.

FIG. 3 is a schematic diagram of a training pipeline for use in an embodiment of the present disclosure. The training pipeline 300 is typically implemented by the processing device 110, and the corresponding methods are implemented by the processor circuitry 111 based on instructions stored in the memory 113. The memory 113 may further include a database structure for storing data required for implementing the training pipeline 300 or denoising methods, such as implementation of a model, utilizing data generated by the training pipeline. In some embodiments, a database may be stored externally and may be accessed by the processing device 110 by way of a network interface.

The methods implemented by the training pipeline 300 include training a learning algorithm, such as a CNN, for denoising low-dose CT images using domain agnostic learning with disentangled feature representations.

Domain adaptation can be defined as transferring knowledge from a given dataset, such as a source labeled dataset, belonging to a source domain, $D_s$, to a target unlabeled dataset that belongs to a specific known target domain $D_t$. Domain agnostic learning is defined in a similar way, except that both the target unlabeled dataset and the source dataset can consist of data from multiple domains (e.g. $\{D_{t1}, D_{t2}, D_{tn}\}$ for target domains and $\{D_{s1}, D_{s2}, D_{sn}\}$ for source domains), without any domain label for each sample annotating which domain it belongs to. Domain agnostic learning may be achieved by using disentangled feature representation learning that disentangles style from content.

As such, the training pipeline 300 disentangles an anatomy feature a from a noise feature n for CT images processed by the pipeline, where the anatomy feature and the noise feature can be used to reconstruct the underlying image. When evaluating denoising performance of a model, radiologists may score images for two qualities, namely structural fidelity and image noise suppression. Structural fidelity is the ability of the image to accurately depict the anatomical structures in the field of view, and image noise shows up as random patterns on the image that detract from image quality. By extracting anatomy features from a reduced quality image and pairing it with a reduced noise level typical of a higher quality image, a model generated by the described training pipeline may thereby provide images that score highly by both metrics.

As shown, the training pipeline 300 includes a standard image module 310 and a reduced quality image module 320. The standard image module 310 includes a standard anatomy encoder $E_n^{CT}$ 330, a standard noise encoder $E_n^{CT}$ 340, and a standard generator GP' 350. A standard image source 360, which may be the CT scanning unit 200 of FIG. 2, or which may be an image database, then provides a standard image 370 to the standard image module 310. Upon receipt, the standard image 370 is provided to the standard anatomy encoder 330 and the standard noise encoder 340.

The standard anatomy encoder 330 then outputs a standard anatomy feature $a^{CT}$ 380, and the standard noise encoder 340 outputs a standard noise feature n CT 390. Both the standard noise feature 390 and the standard anatomy feature 380 may then be provided to the standard generator 350 which can reconstruct the standard image $X_{CT}^{CT}$ 370' from the provided standard anatomy feature 380 and standard noise feature 390. As such, the standard image module 310 can deconstruct a standard image 370 into component features 380, 390, and then reconstruct the standard image 370' from those component features.

The reduced quality image module 320 include components parallel to those discussed with respect to the standard image module 310. Accordingly, the reduced quality image module 320 includes a reduced quality anatomy encoder $E_a^{LDCT}$ 430, a reduced quality noise encoder $E_n^{TDCT}$ 440, and a reduced quality generator $G^{LDCT}$ 450. A reduced quality image source 460 then provides a reduced quality image 470 to the reduced quality image module 320. The reduced quality image source 460 may be the CT scanning unit 200 of FIG. 2, where the parameters discussed above are reconfigured such that the image quality is reduced. This may be based on a reduced radiation dose relative to the acquisition of the standard image 370, for example, resulting in a Low Dose CT scan (LDCT) image. Alternatively, the reduced quality image source 460 may be an image database. Upon receipt, the reduced quality image 470 is provided to the reduced quality anatomy encoder 430 and the reduced quality noise encoder 440.

The reduced quality anatomy encoder then outputs a reduced quality anatomy feature $a^{LDCT}$ 480, and the reduced quality noise encoder 440 outputs a reduced quality noise feature $n^{LDCT}$ 490. Both the reduced quality noise feature 490 and the reduced quality anatomy feature 440 may then be provided to the reduced quality generator 450 which can reconstruct the reduced quality image $X_{LDCT}^{LDCT}$ 470∝ from the provided reduced quality anatomy feature 480 and reduced quality noise feature 490. As such, the reduced quality image module 320 can deconstruct a reduced quality image 470 into component features 480, 490, and then reconstruct the reduced quality image 470' from those component features.

When training the standard image module 310 and the reduced quality image module 320, a loss calculation module 500 is provided to calculate various loss functions. Accordingly, a loss metric for the standard generator 350 may be at least partially based on a comparison between the standard image 370 and the reconstructed standard image 370'. Such a loss metric may be a reconstruction loss 510 for the standard generator 350, and may be used during training to ensure that reconstructions 370' generated by the standard generator are true to the originally provided corresponding standard image 370.

Similarly, a loss metric for the reduced quality generator 450 may be at least partially based on a comparison between the reduced quality image 470 and the reconstructed reduced quality image 470' generated by the reduced quality generator 450. The loss metric may also be a reconstruction loss 520 for the reduced quality generator 450, and may be used during training to ensure that reconstructions 470' from the reduced quality generator are true to the originally provided corresponding reduced quality image 470.

The anatomy encoders 330, 430, are also evaluated by the loss calculation module 500. A loss metric for the standard anatomy encoder 330 may be evaluated based on a comparison between the standard anatomy feature 380 and segmentation labels 540 generated for the corresponding standard image 370. Such segmentation labels may be manually generated when the standard image 370 is acquired, or they may be retrieved from a database. Such a loss metric may be a segmentation loss 530.

A loss metric for the reduced quality anatomy encoder 430 is evaluated based on a comparison between the reduced quality anatomy feature 480 and a standard anatomy feature 380 generated by the standard anatomy encoder 330. While this comparison is discussed in more detail below, with respect to the training method of FIGS. 4A-C, such a loss metric would typically be an adversarial loss 550.

In order to evaluate the anatomy encoders 330, 340, the loss calculation module 500 is provided with a segmentation network 560 which creates segmentation masks $M_a^{CT}$ and $M_a^{LDCT}$ 570a and 570b, respectively, for the corresponding anatomy features 380, 480. The segmentation mask 570a for the standard anatomy feature 480 is then compared to the segmentation labels 540, and the segmentation mask 570b for the reduced quality anatomy feature 480 is then compared to a segmentation mask 570a for the standard anatomy feature 380.

The loss metrics are incorporated into loss functions for tuning the respective generators 350, 450 and anatomy encoders 330, 430 using machine learning. Accordingly, the reconstruction loss 510, 520 for the generators 350, 450, respectively, can be used to improve the performance of their respective pipelines by adjusting variables that determine the output of the corresponding modules. This may be done by implementing standard machine learning techniques, or by implementing the exemplary training method discussed below in reference to FIGS. 4A-C.

In some embodiments, the loss calculation module further generates additional loss metrics. Such loss metrics may include a segmentation loss 580 for the reconstruction of the standard image 370' generated by the standard generator 350. Accordingly, a segmentation network 590 may be applied to the reconstructed image 370' to generate a segmentation mask $M_{CT}^{CT}$ 600, which is then evaluated based on the segmentation labels 540 for the corresponding image 370. The segmentation loss 580 may be considered by any training process used in the training pipeline 500.

As shown, there is a connection between the output anatomy feature 380 of the standard anatomy encoder 330 and the reduced quality generator 450, as well as a connection between the output anatomy feature 480 of the reduced quality anatomy encoder 430 and the standard generator 350. When provided with a standard anatomy feature 380 from the standard anatomy encoder 330, the generator 350 outputs a reconstructed standard image 370' based on the standard anatomy feature and a standard noise feature 390 generated by the standard noise encoder 340. In contrast, when provided with a reduced quality anatomy feature 480 generated by a reduced quality anatomy encoder 430, the standard generator 350 outputs a reconstructed standard transfer image $X_{LDCT}^{CT}$ 470".

The reconstructed standard transfer image 470" includes the reduced quality anatomy feature 480 and a noise level lower than that represented by the reduced quality noise feature 490. This may be constructed by the generator 350 based on the reduced quality anatomy feature 480 and a noise feature 390 generated by the standard noise feature encoder 340. In the case of a transfer image, such noise feature 390 may be, for example, an average of standard noise features generated from corresponding standard images 370 during training.

Similarly, the reduced quality generator 450 may be used to generate transfer images. Accordingly, when the reduced quality generator 450 is provided with a standard anatomy feature 380 from the standard anatomy encoder 330, the generator 350 outputs a reconstructed reduced quality transfer image $X_{CT}^{LDCT}$ 370".

The reconstructed reduced quality transfer image 370" includes the standard anatomy feature 380 and a noise level based on a reduced quality noise feature 490.

In order to further improve the quality of any models implemented using the training pipeline 500, the transfer images 370", 470" may be used to generate additional loss metrics. Accordingly, the reconstructed standard quality transfer image 470" may be evaluated with an adversarial loss 610 for comparing the transfer image to reconstruction images 370' output by the standard generator 350.

Similarly, the reconstructed reduced quality transfer image 370″ may be evaluated using a loss metric. Because the reduced quality transfer image 370″ includes a standard anatomy feature 380, the training pipeline 300 would typically have access to corresponding segmentation labels 540. As such, the loss metric for the reduced quality transfer image 370″ may be the segmentation loss 620, where a segmentation network 630 generates an appropriate segmentation mask $M_{CT}^{LDCT}$ 640.

It is further noted that in some embodiments, the segmentation networks themselves 560, 590, 630 may be evaluated based on segmentation loss 530, 580, 620 as the result of comparisons between the resulting segmentation masks 570a, 580, 620 and the segmentation labels 540.

In some embodiments, the entirety of the training pipeline 300 is trained simultaneously. As such, the standard image module 310 and the reduced quality image module 320 would both be provided with a variety of images for the purpose of training the respective modules. As the network improves, based on the loss metrics, the anatomy features, and the reconstructed images, the training pipeline would be instructed to generate transfer images 470″, 370″ which are then evaluated in parallel.

In contrast, in some embodiments, the training pipeline 300 is trained in sequence, as discussed at length below in reference to FIGS. 4A-C.

The described training pipeline 300 may be used to generate a model for generating transfer images 470″ which can then be used to denoise previously reduced quality images 470. The training pipeline 300 may be used to create modules for transferring anatomy features from a wide variety of source images obtained using different imaging parameters. For example, different encoders may be trained for transferring images obtained using different dosages.

Further, while the same model created using the training pipeline 300 may be used across distinct anatomy features, in some embodiments, usage of a model trained using the pipeline may be limited to a specific anatomical structure. While the reduced quality images 470 would not be of the same patient, or the same organ, as the standard images 370, they would then relate to the same anatomical structure in different images. For example, a model may be trained for images of heads, abdomens, or specific organs.

Figure 4A:
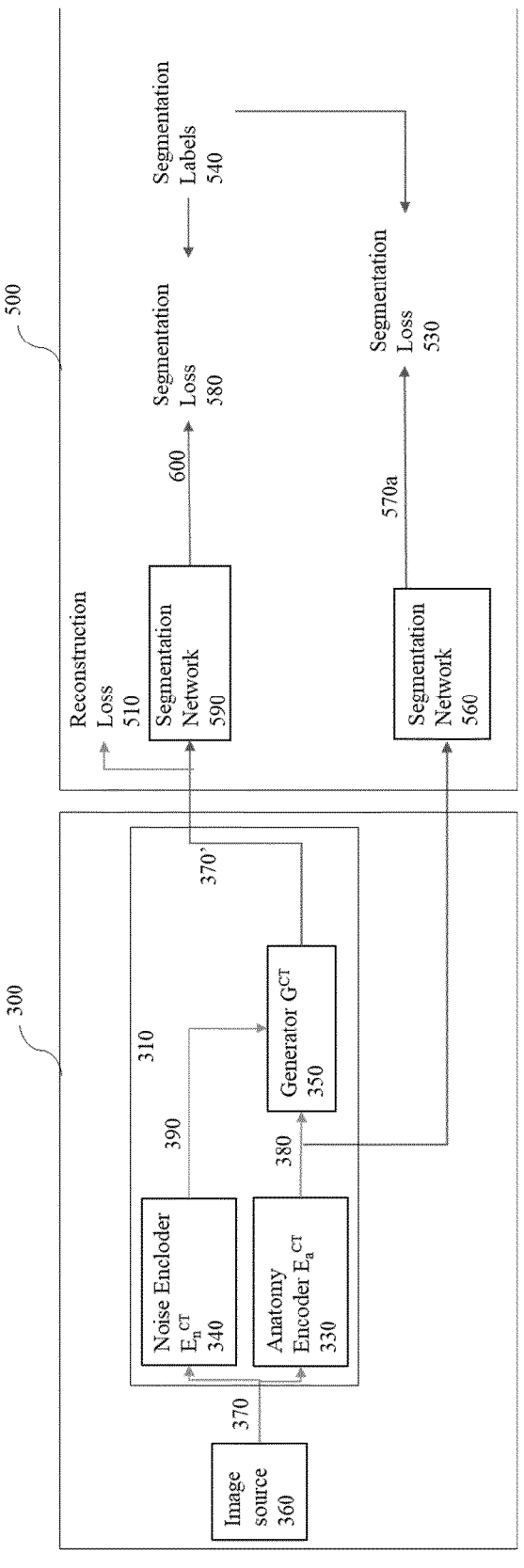
FIGS. 4A-C illustrate an exemplary training method for use with the training pipeline of FIG. 3.
Figure 4B:
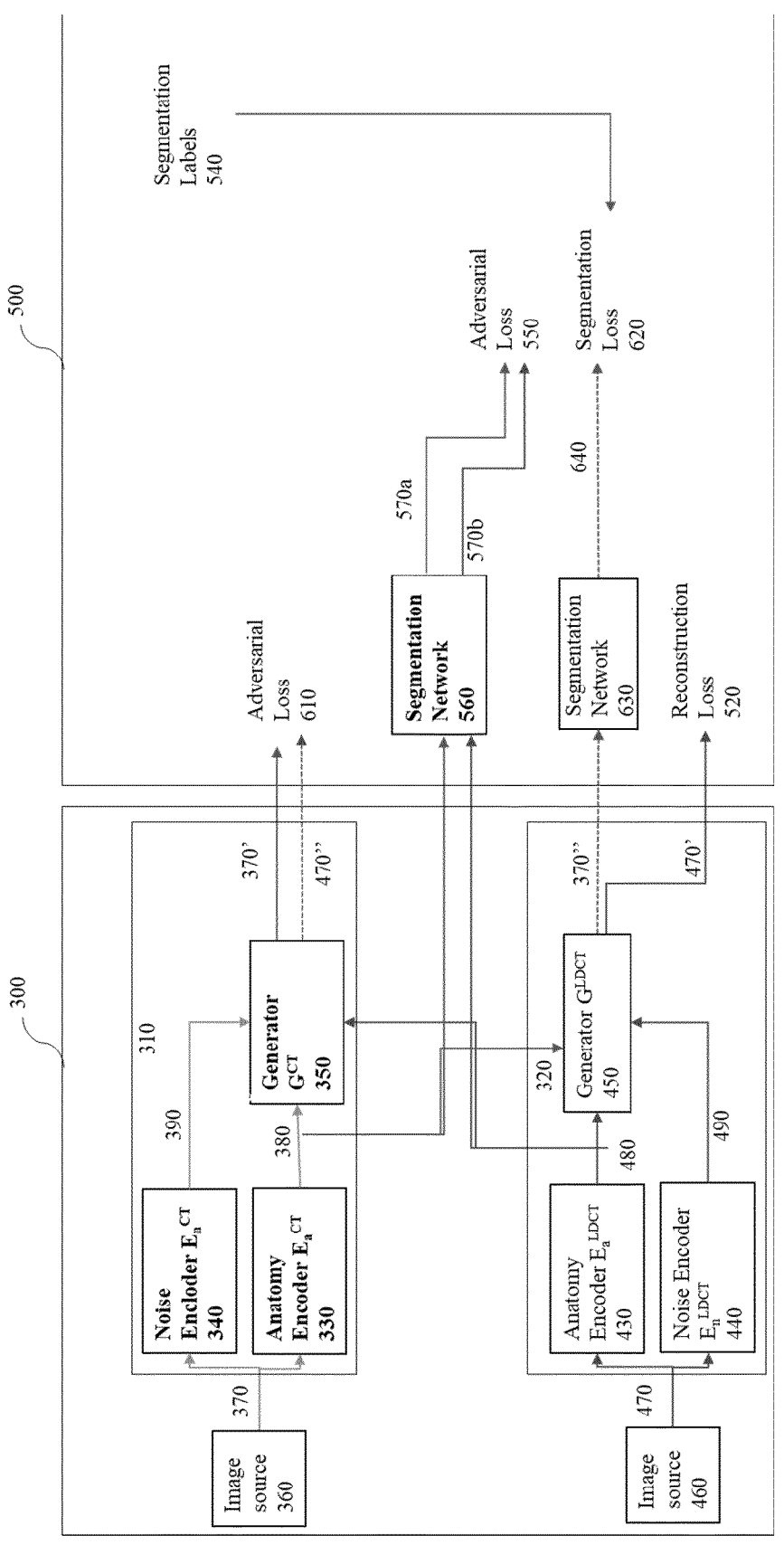
Figure 4C:
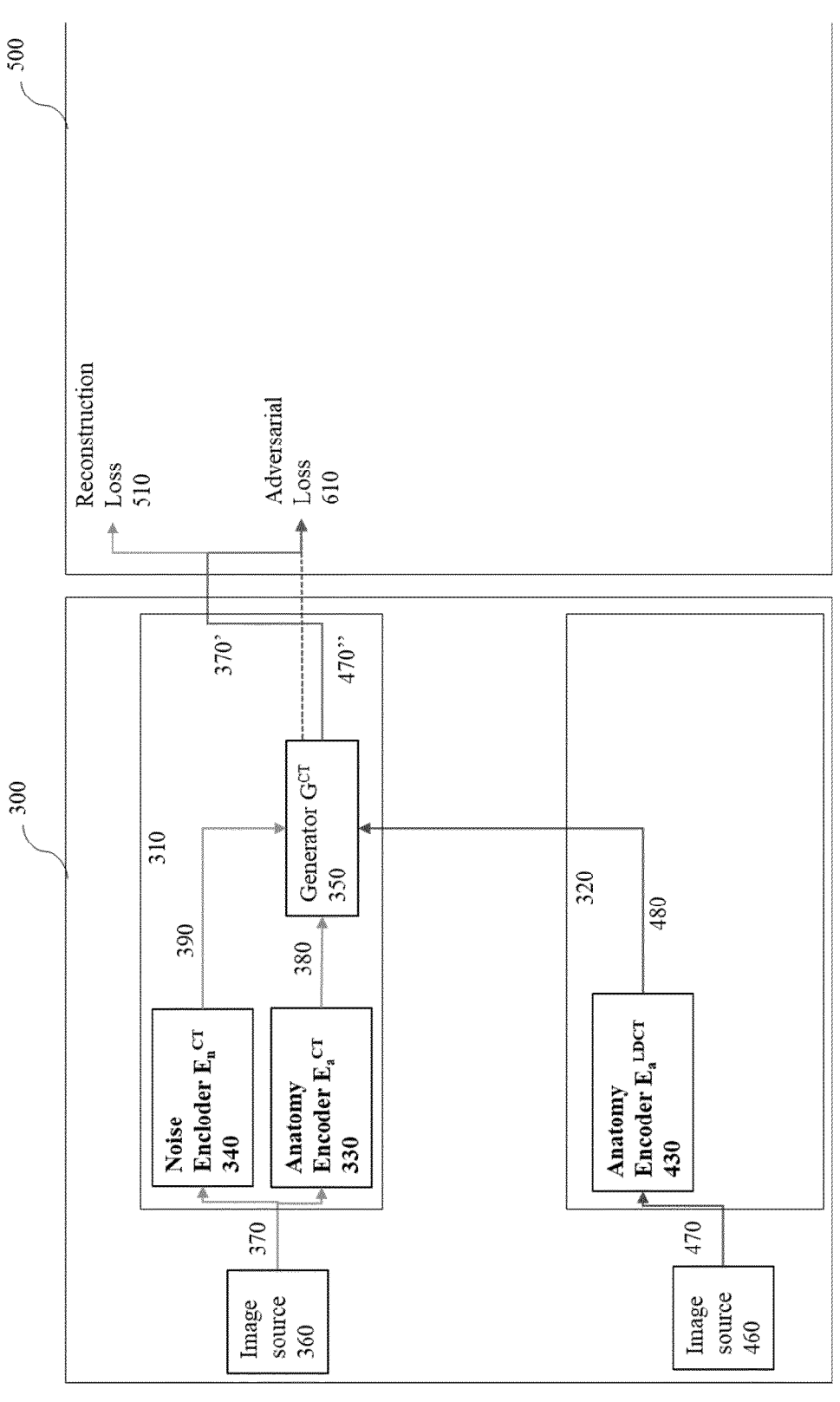

FIGS. 4A-C illustrate an exemplary training method for use with the training pipeline 300 of FIG. 3.

In some embodiments, as shown in FIG. 4A, the standard image module 310 is trained prior to training the reduced quality image module 320. In such embodiments, as shown in FIG. 4B, when training the reduced quality image module 320, variables associated with the standard image module, including those embedded in the standard image encoders 330, 340, those in the standard generator 350, and those in the segmentation network 560 associated with the standard anatomy feature 380, are held constant.

In such an embodiment, after training the standard image module 310 and the reduced quality image module 320 independently, the training pipeline 300 may then further train the standard generator 350 while holding values for the standard anatomy encoder 330, the standard noise encoder 340, and the reduced quality anatomy encoder 430.

Accordingly, when training a model using the claimed method, a method implementing a training pipeline 300 in accordance with this disclosure may initially provide the standard image module 310. The standard image module 310 has a standard anatomy encoder 330 for extracting a standard anatomy feature 380 from a standard image 370 and a standard noise encoder 340 for extracting a standard noise feature 390 from the standard image.

The standard image module 310 also has a standard generator 350 for generating a reconstructed standard image 370′ from the standard anatomy feature 380 and the standard noise feature 390.

The method may then provide the reduced quality image module 320. The reduced quality image module 320 has a reduced quality anatomy encoder 430 for extracting a reduced quality anatomy feature 480 from a reduced quality image 470 and a reduced quality noise encoder 440 for extracting a reduced quality noise feature 490 from the standard image.

The reduced quality image module 410 also has a reduced quality generator 450 for generating a reconstructed reduced quality image 470′ from the reduced quality anatomy feature 480 and the reduced quality noise feature 490.

The standard image module 310 is then trained by receiving, at the standard image module, a plurality of standard images 370. These would be received from an image source 360 which may be a CT scanning unit 200 or may alternatively be a database of images. The system then compares reconstructed standard images 370′ output by the standard image generator 350 for each standard image 370 received to the corresponding standard image to extract a standard reconstruction loss metric. Variables of the standard image module 310 are then updated based on such loss metric, thereby tuning the standard encoders 330, 340 and the standard generator 350.

While still training the standard image module 310, the method generates, at a segmentation network 560, a segmentation mask 570a corresponding to a standard anatomy feature 380 extracted from each standard image 370 by the standard anatomy encoder 330. The segmentation mask 570a for each standard image 370 is then compared to segmentation labels 540 associated with the corresponding standard image 370 to generate a standard anatomy loss metric 530. At least one variable of the standard anatomy encoder 330 is then updated based on the standard anatomy loss metric.

As shown in FIG. 4A, these initial training steps may be performed on a portion of the training pipeline 300 associated with standard images 370 independently of the reduced quality image module 320. Additional training elements may be implemented during this first portion of training to improve the models used for the standard encoders 330, 340 and the standard generator 350. For example, the reconstructed standard images 370′ may be submitted to an additional segmentation network 590 to generate a segmentation mask 600, which may then be compared to the known segmentation labels 540 for the corresponding images 370, thereby generating an additional segmentation loss metric.

After the standard image module 510 has been trained and provides acceptable results, the reduced quality image module 320 may be trained, as shown in FIG. 4B. As such, a plurality of reduced quality images 470 are received at the reduced quality image module 320 from an image source 460. As discussed above, the image source may be a CT scanning unit 200 or an image database, or some combination thereof.

The system then compares reconstructed reduced quality images 470′ output by the reduced quality image generator 450 for each reduced quality image 470 received to the corresponding reduced quality image to extract a reduced quality reconstruction loss 520. Variables of the standard image module 310 are then held constant while variables of the reduced quality image module 320 are updated based on the loss metric, thereby tuning the reduced quality encoders 430, 440 and the reduced quality generator 450.

The segmentation network 560 initially trained when training the standard image module 310 is similarly held constant when training the reduced quality image module 320. The segmentation network 560 is then used to generate a segmentation mask 570b corresponding to a reduced quality anatomy feature 480 extracted from each reduced quality image 470 by the reduced quality anatomy encoder 430. The segmentation mask 570b is then compared to at least one, and typically an average of segmentation masks 570a previously generated by the standard image module 310 to generate an adversarial loss metric.

The adversarial loss metric is then used to update at least one variable of the reduced quality anatomy encoder 430.

Once the reduced quality image module 320 has been trained in this way, the reduced quality anatomy feature 480 generated by the reduced quality anatomy encoder 430 may then be provided to the standard generator 350 in the standard image module 310. The standard generator 350 may then output a reconstructed standard transfer image 470" based on the reduced quality anatomy feature 480 and at least one, and in some cases an average of the standard quality noise features 390.

The reconstructed standard transfer image 470" may then be evaluated by comparing it to a standard image reconstruction 370' or an average of multiple such reconstructions, to generate an adversarial loss 610. While the standard generator 350 is held constant, and therefore would not be tuned based on this loss metric, the reduced quality anatomy encoder 430 may be further tuned on that basis.

Further, as discussed above, the reduced quality generator 450 may be used to generate reconstructed reduced quality transfer images 370". Such transfer images 370" may be based on standard anatomy features 380 generated by the standard image module 320 and may be parsed by a segmentation network 630 to generate corresponding segmentation maps 640, which can then be evaluated against the segmentation labels 540 to generate a segmentation loss 620. This loss metric could then be used to further tune the reduced quality module 320.

In some embodiments, the model created by the described training pipeline 300 may be used to create standard transfer images 470" which can then be denoised. In other embodiments, such as that shown in FIG. 4C, the training pipeline may then be further trained. As shown, the relevant encoders 330, 340, and 430 may be held constant while the standard generator 350 is further tuned. This is done by creating additional reconstructed standard transfer images 470" which can then be compared to one or more standard reconstruction 370' to generate additional adversarial loss data 610, which can then be used to further tune the standard generator 350.

By training the described training pipeline 300 in this way, there are multiple checks in the design that encourage anatomy embedding to be domain agnostic and anatomy preserving.

Figure 5:
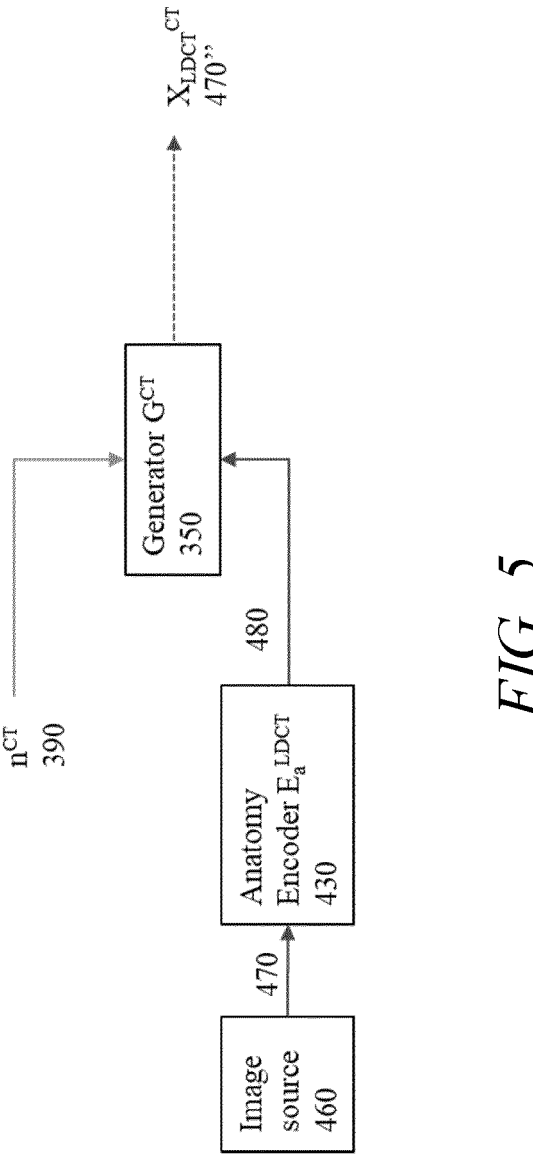
FIG. 5 illustrates the use of a model trained using the training pipeline of FIG. 3 to denoise an image.

FIG. 5 illustrates the use of a model trained using the training pipeline 330 of FIG. 3 to denoise an image. In doing so, the model would first encode the low dose anatomy data from a reduced quality image 470 into a reduced quality anatomy feature 480 using the reduced quality anatomy encoder 430. The reduced quality anatomy feature 480 is then fed with a standard noise feature 390 or an average of such noise features into the standard generator 350 to generate the reconstructed standard transfer image 470".

This training pipeline 300 can be used to train the conversion from low dose CT, or other reduced quality images, to multiple normal dose CT or standard images, with different noise levels. In the case of CT images, these noise levels can represent the overall average of the normal dose CT data, or the average of a group of CT data with certain characteristics, e.g. those reconstructed with a specific algorithm such as filtered back projection or iterative reconstruction. To get these noise features, the trained CT-noise encoder $E_n^{CT}$ 330 is applied to all or a subset of the normal dose CT images 370 in the training set to encode them into CT-noise features 390. Then, the average of these features is taken within each group to obtain their own representative CT-noise feature, $n^{CT1}$, $n^{CT2}$, etc., each of which can then be used as the average noise feature 390 discussed above. To denoise a low dose CT data, a user can choose from the pre-defined CT-noise features 390 based on the specific needs. The training pipeline 300 may also implement interpolation of the CT-noise features extracted from different groups, so that the user can adjust the CT-noise continuously.

It will be understood that although the methods described herein are described in the context of CT scan images, various imaging technology, including various medical imaging technologies are contemplated, and images generated using a wide variety of imaging technologies can be effectively denoised using the methods described herein.

The methods according to the present disclosure may be implemented on a computer as a computer implemented method, or in dedicated hardware, or in a combination of both. Executable code for a method according to the present disclosure may be stored on a computer program product. Examples of computer program products include memory devices, optical storage devices, integrated circuits, servers, online software, etc. Preferably, the computer program product may include non-transitory program code stored on a computer readable medium for performing a method according to the present disclosure when said program product is executed on a computer. In an embodiment, the computer program may include computer program code adapted to perform all the steps of a method according to the present disclosure when the computer program is run on a computer. The computer program may be embodied on a computer readable medium.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

All examples and conditional language recited herein are intended for pedagogical purposes to aid the reader in understanding the principles of the disclosure and the concepts contributed by the inventor to furthering the art, and are to be construed as being without limitation to such specifically recited examples and conditions. Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A system for denoising medical images, comprising:

a standard image module configured to generate a standard anatomy feature and a standard noise feature from a standard image, and reconstruct the standard image from the standard anatomy feature and the standard noise feature;

a reduced quality image module configured to generate a reduced quality anatomy feature and a reduced quality noise feature from a reduced quality image, and reconstruct the reduced quality image from the reduced quality anatomy feature and the reduced quality noise feature;

a loss calculation module configured to calculate loss metrics comprising (i) a first reconstruction loss based at least in part on a comparison between the reconstructed standard image and the standard image; and (ii) a second reconstruction loss based at least in part on a comparison between the reconstructed reduced quality image and the reduced quality image, wherein the first reconstruction loss and the second reconstruction loss are computed independently of each other and are not cross-compared;

wherein the loss metrics are used for tuning the standard image module and the reduced quality image module using machine learning, wherein when the standard image module is provided with the reduced quality anatomy feature, the standard image module outputs a reconstructed standard transfer image that comprises the reduced quality anatomy feature and a noise level lower than that represented by the reduced quality noise feature, and wherein the loss calculation module comprises a standard anatomy encoder and is further configured to calculate a loss metric for the standard anatomy encoder based on a comparison between the standard anatomy feature and segmentation labels for the standard image.

2. The system of claim 1, wherein:

the standard image module comprises a standard noise encoder, and a standard generator, and wherein upon receipt of the standard image, the standard anatomy encoder outputs the standard anatomy feature, the standard noise encoder outputs the standard noise feature, and the standard generator reconstructs the standard image from the standard anatomy feature and the standard noise feature;

the reduced quality image module comprises a reduced quality anatomy encoder, a reduced quality noise encoder, and a reduced quality generator, and wherein upon receipt of the reduced quality image, the reduced quality anatomy encoder outputs the reduced quality anatomy feature, the reduced quality noise encoder outputs the reduced quality noise feature, and the reduced quality generator reconstructs the reduced quality image from the reduced quality anatomy feature and the reduced quality noise feature;

wherein the loss calculation module calculates a loss metric for the standard generator at least partially based on the comparison between the reconstructed standard image and the standard image;

wherein the loss calculation module calculates a loss metric for the reduced quality generator at least partially based on the comparison between the reconstructed reduced quality image and the reduced quality image;

and wherein the loss calculation module calculates a loss metric for the reduced quality anatomy encoder based on a comparison with the output of the standard anatomy encoder.

3. The system of claim 2, wherein the loss metric for the reduced quality anatomy encoder is an adversarial loss metric.

4. The system of claim 1 further comprising a segmentation network, and wherein a segmentation mask for the reconstructed standard image is evaluated based on a comparison with segmentation labels for the standard image.

5. The system of claim 4, wherein when the reduced quality generator is provided with a standard anatomy feature, the reduced quality generator outputs a reconstructed reduced quality transfer image that comprises the standard anatomy features and a noise level higher than that represented by the standard noise feature, and wherein a segmentation mask for the reduced quality transfer image is evaluated based on a comparison with the segmentation labels for the standard image.

6. The system of claim 1, wherein a loss metric for the standard transfer image is evaluated based on a comparison with a standard image reconstruction, and wherein the loss metric for the standard transfer image is an adversarial loss metric.

7. The system of claim 1 wherein the standard image module and the reduced quality image module are trained simultaneously.

8. The system of claim 1, wherein the standard image module is trained prior to the training of the reduced quality image module, and wherein values for variables developed while training the standard image module are held constant during training of the reduced quality image module.

9. The system of claim 8, wherein after training the standard image module and the reduced quality image module, the system further trains the standard generator while holding constant values for the standard anatomy encoder, the standard noise encoder, and the reduced quality anatomy encoder.

10. The system of claim 1, wherein the standard anatomy feature and the reduced quality anatomy feature each correspond to a single anatomical structure.

11. A method for denoising medical images, comprising:

generating, by a standard image module, a standard anatomy feature and a standard noise feature from a standard image;

reconstructing, by a standard image module, the standard image from the standard anatomy feature and the standard noise feature;

generating, by a reduced quality image module, a reduced quality anatomy feature and a reduced quality noise feature from a reduced quality image;

reconstructing, by the reduced quality image module, the reduced quality image from the reduced quality anatomy feature and the reduced quality noise feature; and calculating, by a loss calculation module, loss metrics comprising (i) a first reconstruction loss based at least in part on a comparison between the reconstructed standard image and the standard image; and (ii) a second reconstruction loss based at least in part on a comparison between the reconstructed reduced quality image and the reduced quality image, wherein the first reconstruction loss and the second reconstruction loss are computed independently of each other and are not cross-compared;

wherein the loss metrics are used for tuning the standard image module and the reduced quality image module using machine learning, wherein when the standard image module is provided with the reduced quality anatomy feature, the standard image module outputs a reconstructed standard transfer image that comprises the reduced quality anatomy feature and a noise level lower than that represented by the reduced quality noise feature, and wherein the loss calculation module comprises a standard anatomy encoder and is further configured to calculate a loss metric for the standard anatomy encoder based on a comparison between the standard anatomy feature and segmentation labels for the standard image.

12. The method of claim 11, wherein:

the standard image module comprises a standard noise encoder, and a standard generator, and wherein upon receipt of the standard image, the standard anatomy encoder outputs the standard anatomy feature, the standard noise encoder outputs the standard noise feature, and the standard generator reconstructs the standard image from the standard anatomy feature and the standard noise feature;

the reduced quality image module comprises a reduced quality anatomy encoder, a reduced quality noise encoder, and a reduced quality generator, and wherein upon receipt of the reduced quality image, the reduced quality anatomy encoder outputs the reduced quality anatomy feature, the reduced quality noise encoder outputs the reduced quality noise feature, and the reduced quality generator reconstructs the reduced quality image from the reduced quality anatomy feature and the reduced quality noise feature;

wherein the loss calculation module calculates a loss metric for the standard generator at least partially based on the comparison between the reconstructed standard image and the standard image;

wherein the loss calculation module calculates a loss metric for the reduced quality generator at least partially based on the comparison between the reconstructed reduced quality image and the reduced quality image;

and wherein the loss calculation module calculates a loss metric for the reduced quality anatomy encoder based on a comparison with the output of the standard anatomy encoder.

13. The method of claim 12, wherein the loss metric for the reduced quality anatomy encoder is an adversarial loss metric.

14. The method of claim 11 further comprising generating a segmentation mask for the reconstructed standard image at a segmentation network and evaluating the segmentation mask based on a comparison with segmentation labels for the standard image.

15. The method of claim 14 wherein, upon providing the reduced quality generator with a standard anatomy feature, the reduced quality generator outputs a reconstructed reduced quality transfer image, the reduced quality transfer image including the standard anatomy features and a noise level higher than that represented by the standard noise feature, and wherein a segmentation mask for the reduced quality transfer image is evaluated based on a comparison with the segmentation labels for the standard image.

16. The method of claim 11, wherein a loss metric for the standard transfer image is evaluated based on a comparison with a standard image reconstruction, and wherein the loss metric for the standard transfer image is an adversarial loss metric.

17. The method of claim 11 wherein the standard image module and the reduced quality image module are trained simultaneously.

18. The method of claim 11, wherein the standard image module is trained prior to the training of the reduced quality image module, and wherein values for variables developed while training the standard image module are held constant during training of the reduced quality image module.

19. The method of claim 18, wherein after training the standard image module and the reduced quality image module, the method further trains the standard generator while holding constant values for the standard anatomy encoder, the standard noise encoder, and the reduced quality anatomy encoder.

20. The method of claim 11, wherein the standard anatomy feature and the reduced quality anatomy feature each correspond to a single anatomical structure.

* * * * *